United States Patent
Faoro et al.

(10) Patent No.: US 7,201,755 B2
(45) Date of Patent: *Apr. 10, 2007

(54) APPARATUS FOR THE PREPARATION OF A FEMORAL CONDYLE

(75) Inventors: Francisco Faoro, Zurich (CH); Tom Overes, Winterthur (CH)

(73) Assignee: Zimmer GmbH, Winterthur (CH)

( * ) Notice: Subject to any disclaimer, the term of this patent is extended or adjusted under 35 U.S.C. 154(b) by 299 days.

This patent is subject to a terminal disclaimer.

(21) Appl. No.: 10/822,122

(22) Filed: Apr. 9, 2004

(65) Prior Publication Data

US 2004/0249386 A1    Dec. 9, 2004

(30) Foreign Application Priority Data

Apr. 25, 2003   (EP) ................... 03009438

(51) Int. Cl.
*A61F 2/38* (2006.01)
(52) U.S. Cl. ..................................... 606/88
(58) Field of Classification Search ............. 606/87–88
See application file for complete search history.

(56) References Cited

U.S. PATENT DOCUMENTS

| | | | |
|---|---|---|---|
| 4,349,018 A | 9/1982 | Chambers | |
| 4,759,350 A | 7/1988 | Dunn et al. | |
| 5,342,367 A | 8/1994 | Ferrante et al. | |
| 5,364,402 A | 11/1994 | Mumme et al. | |
| 5,643,272 A * | 7/1997 | Haines et al. | 606/80 |
| 5,681,320 A * | 10/1997 | McGuire | 606/104 |
| 6,575,980 B1 * | 6/2003 | Robie et al. | 606/88 |
| 6,695,848 B2 * | 2/2004 | Haines | 606/79 |
| 2003/0100906 A1 * | 5/2003 | Rosa et al. | 606/86 |
| 2004/0249387 A1 * | 12/2004 | Faoro | 606/88 |

FOREIGN PATENT DOCUMENTS

| | | |
|---|---|---|
| DE | 203 03 498 U1 | 8/2003 |
| EP | 0 709 061 A1 | 5/1996 |
| EP | 0 809 969 A2 | 12/1997 |
| FR | 2 679 766 A1 | 2/1993 |
| WO | WO 01/66021 A1 | 9/2001 |
| WO | WO 01/85038 A1 | 11/2001 |

* cited by examiner

*Primary Examiner*—Eduardo C. Robert
*Assistant Examiner*—Michael J. Araj
(74) *Attorney, Agent, or Firm*—Baker & Daniels LLP (57) ABSTRACT

An apparatus for the preparation of a femoral condyle for the insertion of monocondylar knee implants. In one embodiment, at least one combined cutting and drilling jig can be fixed to the femoral condyle, when the knee is in flexion, at a desired spacing from a tibia plateau dependent on the thickness of a tibia implant to be inserted. The jig can include a concave side facing the femoral condyle and curved in accordance with a femur implant to be inserted. The jig can further include at least one fixing passage in a drilling section of the jig for a drill and for a fixing element, with the fixing passage being positioned and orientated with respect to a curved side in accordance with the femur implant to be inserted. The jig includes at least one slot in a cutting section of the jig for a cutting tool by which a cutting plane for a condylar cut is defined and having a coupling section for an aligning aid by means of which the cutting and drilling jig located at the desired spacing from the tibia plateau can be adjusted relative to the femoral condyle.

18 Claims, 11 Drawing Sheets

APPARATUS FOR THE PREPARATION OF A FEMORAL CONDYLE

CROSS-REFERENCE TO RELATED APPLICATION

This application claims priority of EPO Patent Application No. 03 009 438.7 filed Apr. 25, 2003.

The invention relates to an apparatus for the preparation of a femoral condyle for the insertion of monocondylar knee implants.

When monocondylar, i.e. one-sided, knee prostheses are inserted, the condyles of the tibia and of the femur must be prepared in order to create contact surfaces on the bone which ensure a defined position of the tibia and femur implants of the knee prosthesis.

The contact surfaces are produced by cutting away bone material at the condyles. In this process, one endeavors to remove as little bone material as possible. Furthermore, care must be taken that the cut surfaces at the tibia and at the femur are correctly oriented relative to one another so that the tibia and femur implants can cooperate in a manner corresponding to the natural movement of the remaining, healthy part of the knee joint.

When, in the course of a knee operation, the tibia is prepared first and, in this process, a tibia plateau is produced onto which a tibia implant is later mounted, it is important on the preparation of the corresponding femoral condyle that the cut surfaces to be produced on the femoral condyle are correctly aligned relative to the cut surfaces produced at the tibia plateau.

It is the object of the invention to provide an apparatus of the initially named kind with which a femur implant can be implanted at the femur in a manner which is as simple and as reliable as possible in the correct position relative to the tibia with an accuracy which is as high as possible.

This object is satisfied by the features of claim 1 and in particular in that at least one combined cutting and drilling jig is provided which can be fixed to the femoral condyle, when the knee is in flexion, at a desired spacing from a tibia plateau dependent on the thickness of a tibia implant to be inserted, the jig having a concave side facing the femoral condyle and being curved in accordance with a femur implant to be inserted, having at least one fixing passage in a drilling section of the jig for a drill and for a fixing element, with the fixing passage being positioned and orientated with respect to the curved side in accordance with the femur implant to be inserted, having at least one slot for a cutting tool in a cutting section of the jig by which a cutting plane for a condylar cut is defined and having a coupling section for an aligning aid by means of which the cutting and drilling jig located at the desired spacing from the tibia plateau can be adjusted relative to the femoral condyle.

A multifunctional instrument is created with the combined cutting and drilling jig in accordance with the invention with which, on the preparation of the femoral condyle, the femur implant to be implanted on it is simulated insofar as the concave side of the jig is curved in accordance with the femur implant and the fixing passage of the jig likewise corresponds to the femur implant with respect to the position and the orientation relative to the curved side. The cuts and bores to be carried out by means of the cutting and drilling jig in accordance with the invention are consequently ideally matched to the actual femur implant, and indeed also with respect to the position and to the orientation relative to the tibia plateau, since—in accordance with the invention—the cuts and bores can be carried out at the correct desired spacing from the tibia plateau and, moreover, an additional adjustment possibility exists relative to the femoral condyle by the coupling section provided for the alignment aid. This additional adjustment possibility permits a particularly exact alignment of the combined cutting and drilling jig in dependence on the respective anatomical circumstances.

Advantageous embodiments of the invention are recited in the dependent claims, in the description and in the drawing.

At least one coupling passage formed in the drilling section of the jig and extending substantially perpendicular to the fixing passage can be provided as a coupling section. A lateral coupling of the alignment aid is hereby made possible.

In a particularly preferred embodiment, the cutting and drilling jig can be coupled to a spreading device by means of which a desired spacing can be set between the femoral condyle and an oppositely disposed tibia plateau.

By means of a such a spreading device, by spreading open the knee, i.e. by enlarging the spacing between the femur and the tibia, the femur and the tibia can be brought into their natural relative position during the knee operation, with this natural relative position being able to be determined by the surgeon with reference to the natural tension of the ligaments. The spreading device is preferably made such that the cutting and drilling jig in accordance with the invention can be coupled to the spreading device such that the cutting and drilling jig is vertically adjustable relative to the spreading device, and indeed with the knee spread open by means of the spreading device, i.e. with a set desired spacing between the tibia and the femur.

The spreading device itself is not the subject of the present invention so that details with respect to it are not considered more closely in the following.

In a further embodiment of the invention, the cutting section of the cutting and drilling jig is simultaneously made as a slide attachment shoe which can be coupled to the spreading device and via which the cutting and drilling jig is adjustable in a compulsorily guided manner at the spreading device.

Provision can furthermore be made for the cutting and drilling jig to be provided with, in addition to the fixing passage, a positioning passage which is formed in the drilling section of the jig and via which the cutting and drilling jig is positionable relative to the femoral condyle by means of a positioning pin before the fixing to the femoral condyle taking place via the fixing passage.

In a further embodiment of the invention, an additional cutting jig is provided to which the cutting and drilling jig can be coupled and with which, when the knee is in flexion, a further condylar cut can be fixed which extends in a curved manner between two planar cut surfaces previously made at the femoral condyle of which the one cut surface was made by means of the cutting section of the combined cutting and drilling jig and the other cut surface was made when the knee was in extension. The two planar cut surfaces preferably run at least substantially perpendicular to one another.

Provision is furthermore preferably made for the course of the curved side of the combined cutting and drilling jig to be able to be mapped at least regionally on the femoral condyle by means of the additional cutting jig. Since the cutting and drilling jig is shaped at its curved side in accordance with the actual femur implant, the femoral condyle can be precisely matched to the corresponding side of the femur implant by the cooperation of the cutting and drilling jig with the additional cutting jig.

The additional cutting jig can include a disk cam with a convex guide surface along which a cutting tool is guidable and whose extent corresponds to the curved side of the combined extent cutting and drilling jig.

Provision can furthermore be made in accordance with the invention for the additional cutting jig to be oriented with respect to the cutting and drilling jig in the state coupled to the cutting and drilling jig fixed to the femoral condyle such that the guide surface of the additional cutting jig and the curved side of the cutting and drilling jig are only translatorily offset toward one another.

The additional cutting jig can furthermore be made such that it can like-wise be fixed to the femoral condyle in the state coupled to the cutting and drilling jig fixed to the femoral condyle.

It is furthermore proposed in accordance with the invention that the additional cutting jig is provided with at least one fixing passage, and preferably a plurality of fixing passages, which extend substantially perpendicular to the fixing passage of the combined cutting and drilling jig in the state coupled to the combined cutting and drilling jig.

In accordance with a further improved embodiment of the invention, the guide surface is adjustable relative to the femoral condyle with the additional cutting jig fixed to the femoral condyle. This adjustability of the additional cutting jig makes it possible, as required, to carry out a last re-adjustment of the guide surface before the further condylar cut is made.

The additional cutting jig can include a base section which can be fixed to the femoral condyle and to which the disk cam is adjustably attached with the base section fixed to the femoral condyle for the alignment of the guide surface formed at the cam disk with a condylar cut which was previously carried out, when the knee is in extension, at a desired spacing from the tibia plateau dependent on the thickness of a tibia implant to be inserted.

In this process, the disk cam can be adjustable relative to the base section fixed to the femoral condyle such that the vertex of the guide surface formed at the cam disk is disposed in the plane defined by the condylar cut.

It is furthermore proposed in accordance with the invention that the coupling section of the combined cutting and drilling jig provided for the alignment aid is simultaneously made for coupling to the additional cutting jig.

Provision is made in accordance with a further embodiment of the invention for a separate coupling device to be provided for the coupling of the additional cutting jig to the combined cutting and drilling jig at which the additional cutting jig can be fixed and with which the additional cutting jig is adjustable, in particular linearly displaceable, relative to the combined cutting and drilling jig in the fixed state.

The coupling device can include a clamping apparatus by means of which the additional cutting jig can be fixingly clamped to the coupling device.

Furthermore, the coupling device is preferably made such that it can be removed when both the combined cutting and drilling jig and the additional cutting jig are fixed to the femoral condyle.

Both the combined cutting and drilling jig and the additional cutting jig are preferably each provided in different sizes which correspond to differently sized femur implants. Consequently, in dependence on the size of the femur implant selected in accordance with the surgery plan, the respective piece matched size-wise to the femur implant to be inserted is selected from the set of differently sized cutting and drilling jigs and from the set of differently sized additional cutting jigs, whereby a precise preparation of the femoral condyle for the insertion of the femur implant is ensured.

The invention will be described in the following by way of example with reference to the drawing. There are shown.

Figures 7A, 7B:
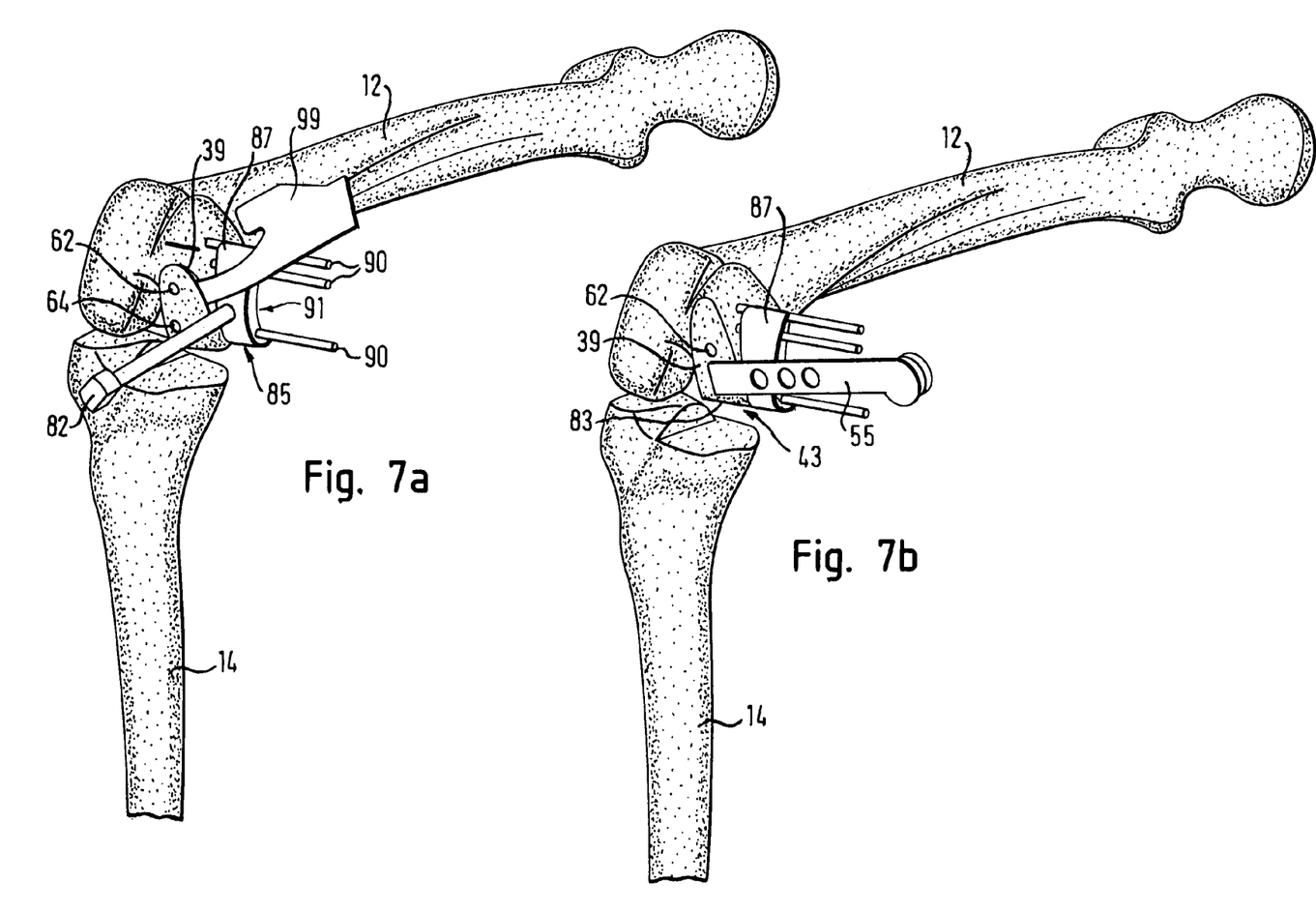
Figure 8:
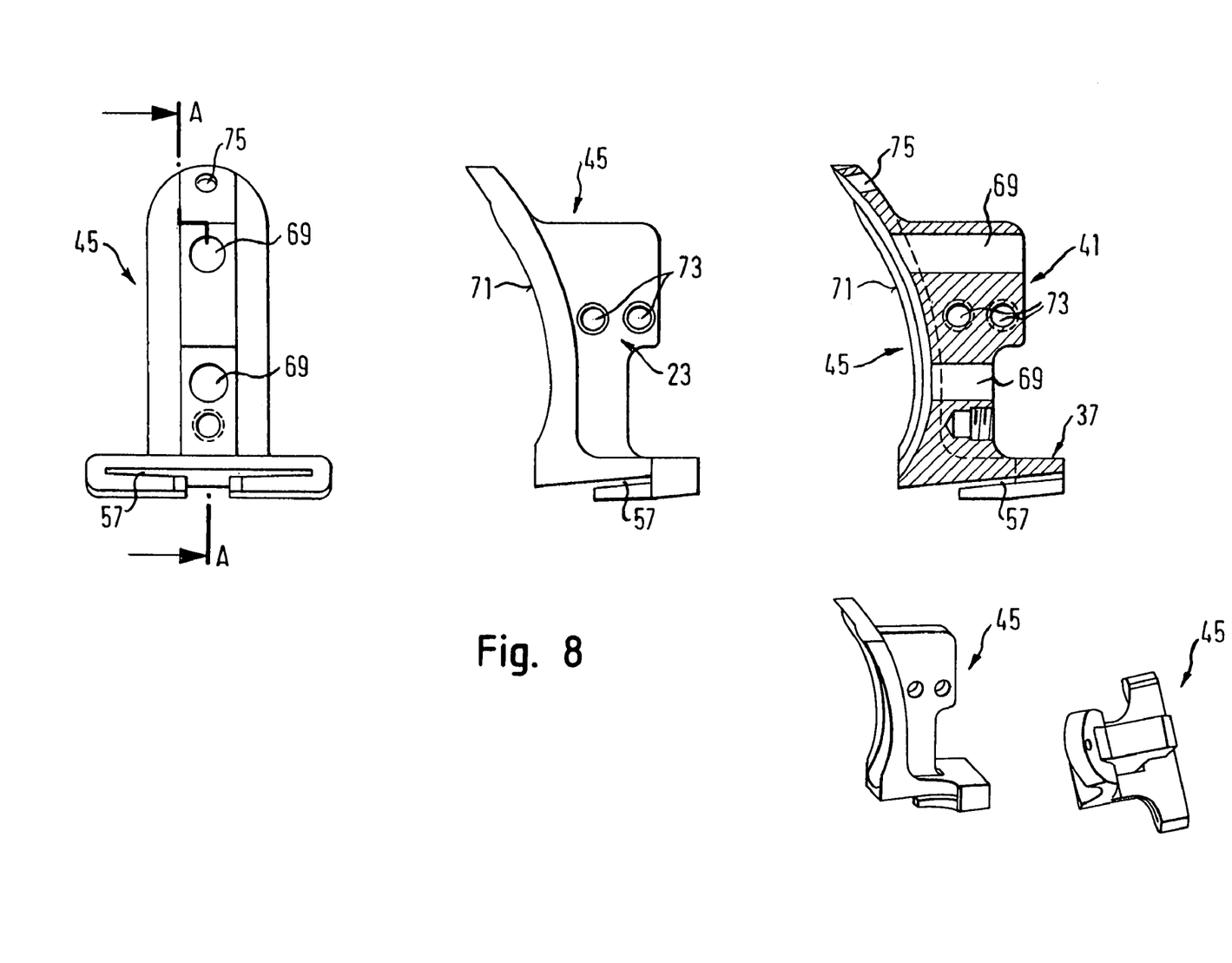
FIG. 8 different views of a combined cutting and drilling jig in accordance with an embodiment of the invention.

Before constructive details of the apparatus in accordance with the invention are considered with reference to FIGS. 8 to 10, that part of a knee operation should first be explained with reference to FIGS. 1 to 7 and 11 in which the apparatus in accordance with the invention is used.

The operation in which the apparatus in accordance with the invention is used in accordance with the embodiment shown in the Figures is a uni-compartmental operation in which the tibial condyle and the femoral condyle are prepared either in the lateral compartment or in the medial compartment for insertion of a tibia implant or of a femur implant.

The starting point for that part of the operation in which the apparatus in accordance with the invention is used, is a tibia plateau which is established by two bone cuts extending perpendicular to one another and onto which a tibia implant provided in accordance with the surgery plan can be mounted as soon as the oppositely lying femoral condyle has also been prepared with the aid of the apparatus in accordance with the invention for the fixing of the corresponding femur implant.

The set of instruments in accordance with the invention includes, in accordance with the embodiment described in the following, a combined cutting and drilling jig 45 which is made in one piece and which includes a drilling section 41 of the jig and a cutting section 37 of the jig.

Subsequently to the establishing of the tibia plateau, which takes place with the knee in extension, a first condylar cut 39 extending parallel to the tibia plateau is first carried out with the knee likewise in extension. This is done by means of a spreading device 11 which is also used in conjunction with the combined cutting and drilling jig 45 in accordance with the invention (cf. FIG. 1). Instead of the cutting and drilling jig 45 in accordance with the invention, another functional attachment is coupled to the spreading device 11 to carry out the first condylar cut 39 when the knee is in extension, said functional attachment including a cutting jig by which the cutting plane for the first condylar cut 39 is defined.

Figure 1:
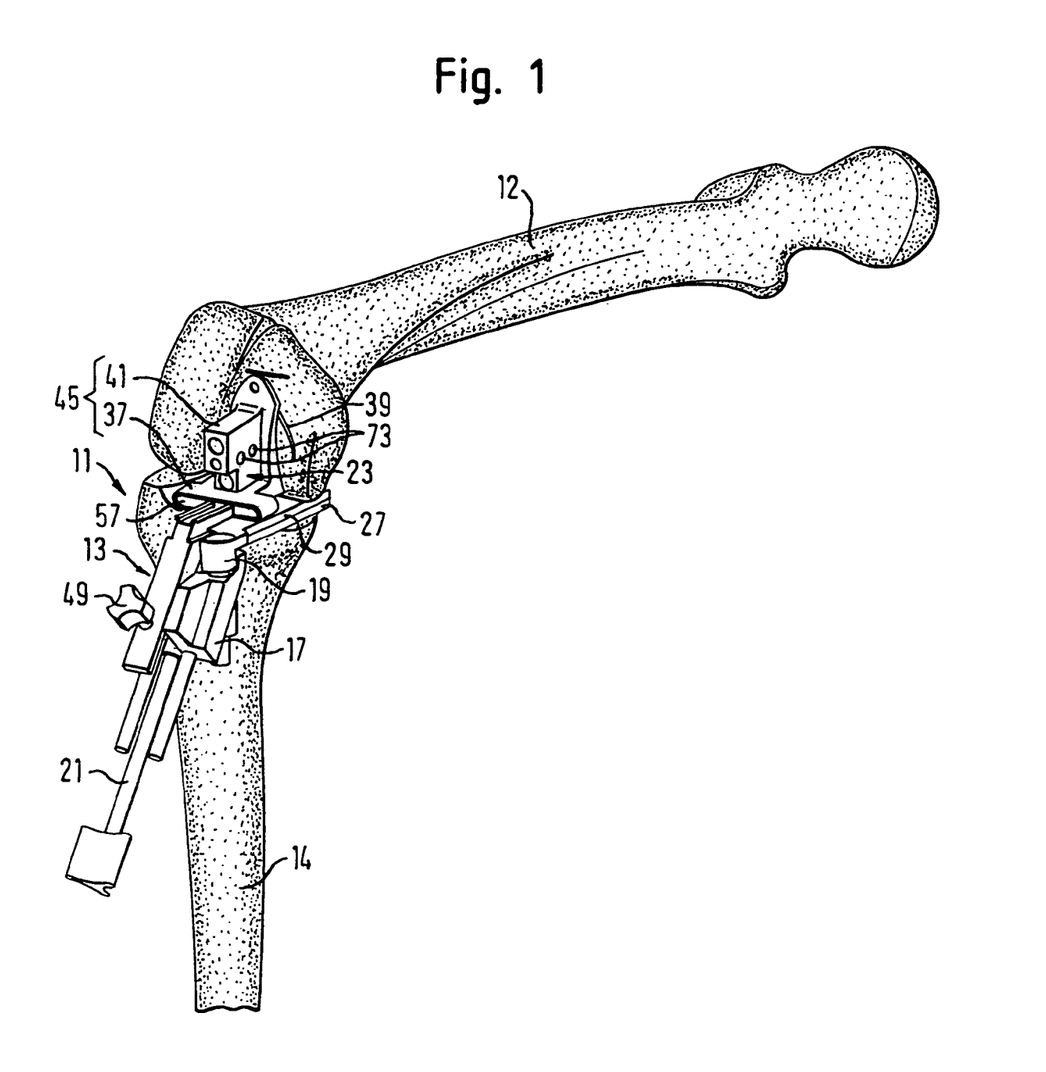
FIGS. 1 to 7 and 11 different phases of part of a knee operation in which a femoral condyle is prepared for the insertion of a femur implant by means of an apparatus in accordance with the invention.

The knee is spread open, i.e. the spacing between the tibia 14 and the femur 12 is increased, with the spreading device 11 until the femur 12 and the tibia 14 have been brought into their natural relative position which the surgeon can determine with reference to the natural tension of the ligaments. It is hereby ensured that the first femoral condylar cut 39 is carried out at the right height above the tibia plateau.

Figure 2:
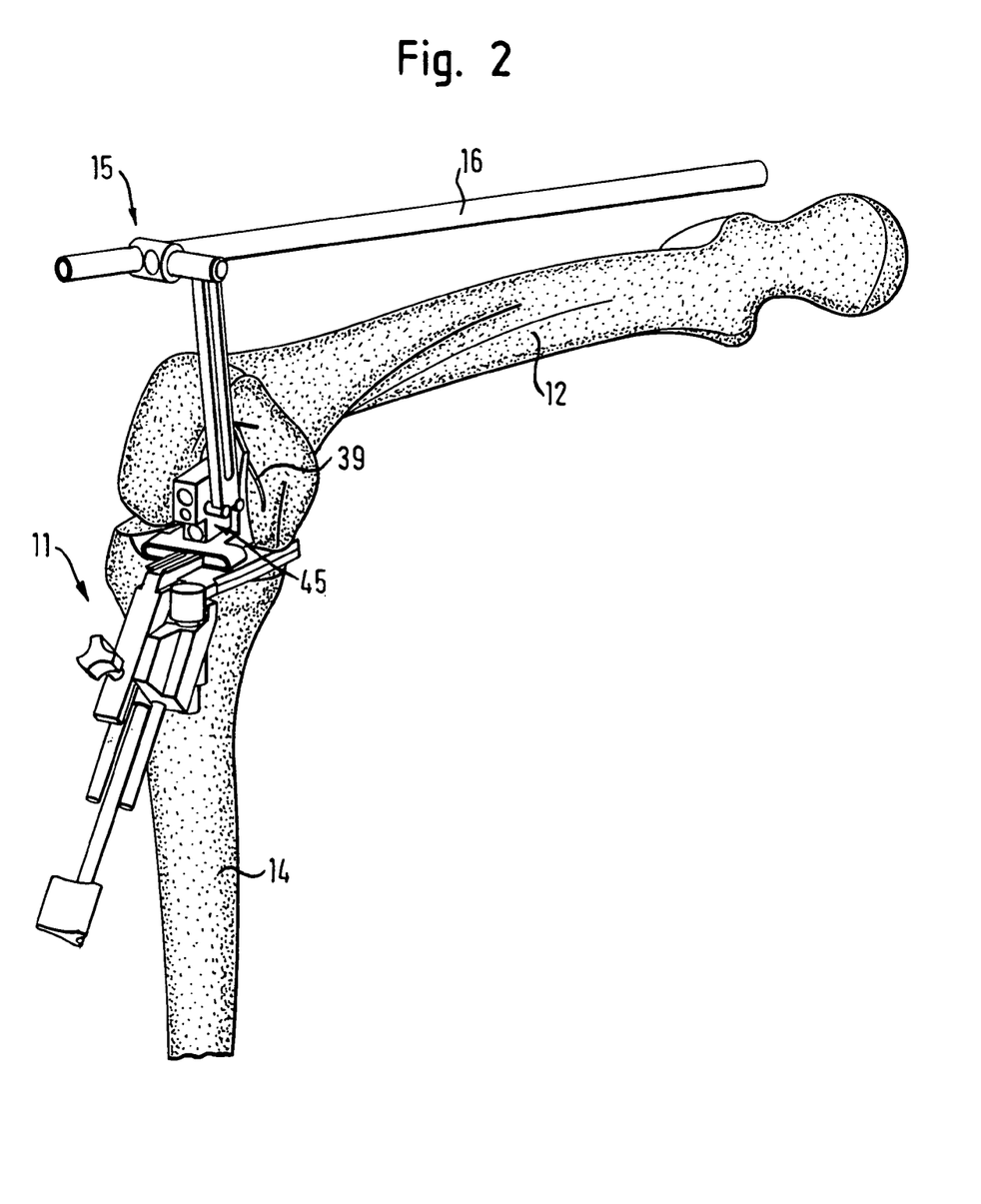
Figure 3:
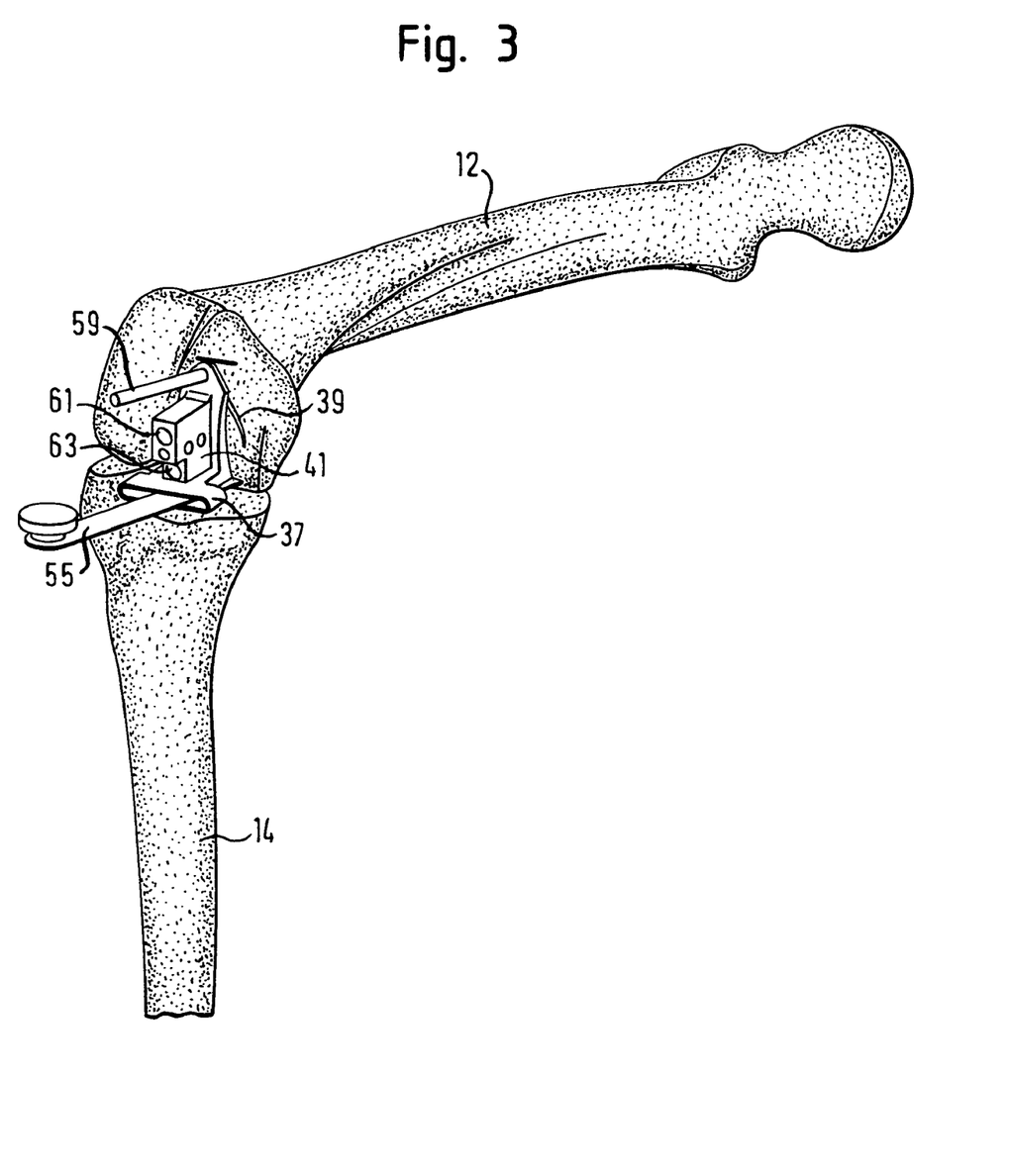

It is accordingly ensured by the spreading device 11, when the knee is in flexion in accordance with FIGS. 1 and 2, that the tibia 14 and the femur 12 adopt their correct relative positions to one another and thus the cutting and drilling jig 45, which is releasably couplable to a functional attachment 13 attached in a vertically adjustable manner to the spreading device 11 can be brought into a desired spacing from the tibia plateau, which can be read off at the spreading device 11, on the correct relative position between the femur 12 and the tibia 14.

The spreading device 11 includes an upper part 19 with a plate-shaped spreading tongue 29 and a lower part 17 with a likewise plate-shaped spreading tongue 27. The femoral condyle can be pressed away from the tibia plateau by means of the two spreading tongues 27, 29 extending parallel to one another in that the upper part 19 is raised with respect to the lower part 17 by means of an actuation member 21 formed as an adjustable screw.

After the cutting and drilling jig 45 in accordance with the invention has been brought into the correct height above the tibia plateau by adjusting the functional attachment 13 relative to the spreading device 11 subsequent to the spreading open of the knee, the functional attachment 13 is fixed to the spreading device 11 by means of a fixing device 49. The cutting and drilling jig 45 displaceably guided on a head section of the functional attachment 13 is thereupon pushed toward and onto the femoral condyle.

Before the cutting and drilling jig 45 is fixed to the femoral condyle, it is aligned relative to the femur 12 by means of an alignment aid 15 (cf. FIG. 2). For this purpose, the jig 45 can be rotated together with the spreading device 11 by means of the alignment aid 15 about an axis extending substantially perpendicular to the tibia plateau. It is moreover possible to displace the jig 45 together with the spreading device 11 parallel to the tibia plateau.

The alignment can also take place visually in that a 90° angle to an abutment metal sheet (e.g. to the metal sheet 99 shown in FIG. 7a and in FIG. 11, which is used for another purpose in FIG. 7a) inserted into the slot 39 is set by the drilling section 41 of the jig. A further alignment possibility in accordance with FIG. 11 consists of inserting into the coupling passages 73 of the drilling section 41 of the jig a 90° angle plate 100 which is provided with pins 101, in which is cut-out in the corner facing the knee during use and which makes a control of the gap to the abutment metal sheet 99 for parallelism relatively simple.

The alignment aid 15, which includes a multi-part linkage with an adjustment rod 16 alignable at the femur 12, can be inserted laterally into two coupling passages 73 formed in the drilling section 41 of the jig 45 and together forming a coupling section 23 of the jig 45.

Subsequently, the correctly aligned jig 45 is positioned at the femoral condyle by means of a positioning pin 59 (cf. FIG. 3) guided through a positioning passage of the jig 45, whereupon bores for fixing elements 61, 63 which are provided in the form of bone screws and by means of which the jig 45 is secured to the femoral condyle are established in the femoral condyle via fixing passages formed in the jig 45.

The spreading device 11 is then removed and a second condylar cut 43 (cf. FIG. 4) is carried out by means of a cutting tool in the form of a saw blade 55 guided through a slot 57 formed in the cutting section 37 of the jig, said second condylar cut extending substantially parallel to the tibia plateau and thus substantially perpendicular to the first condylar cut 39.

Figure 4:
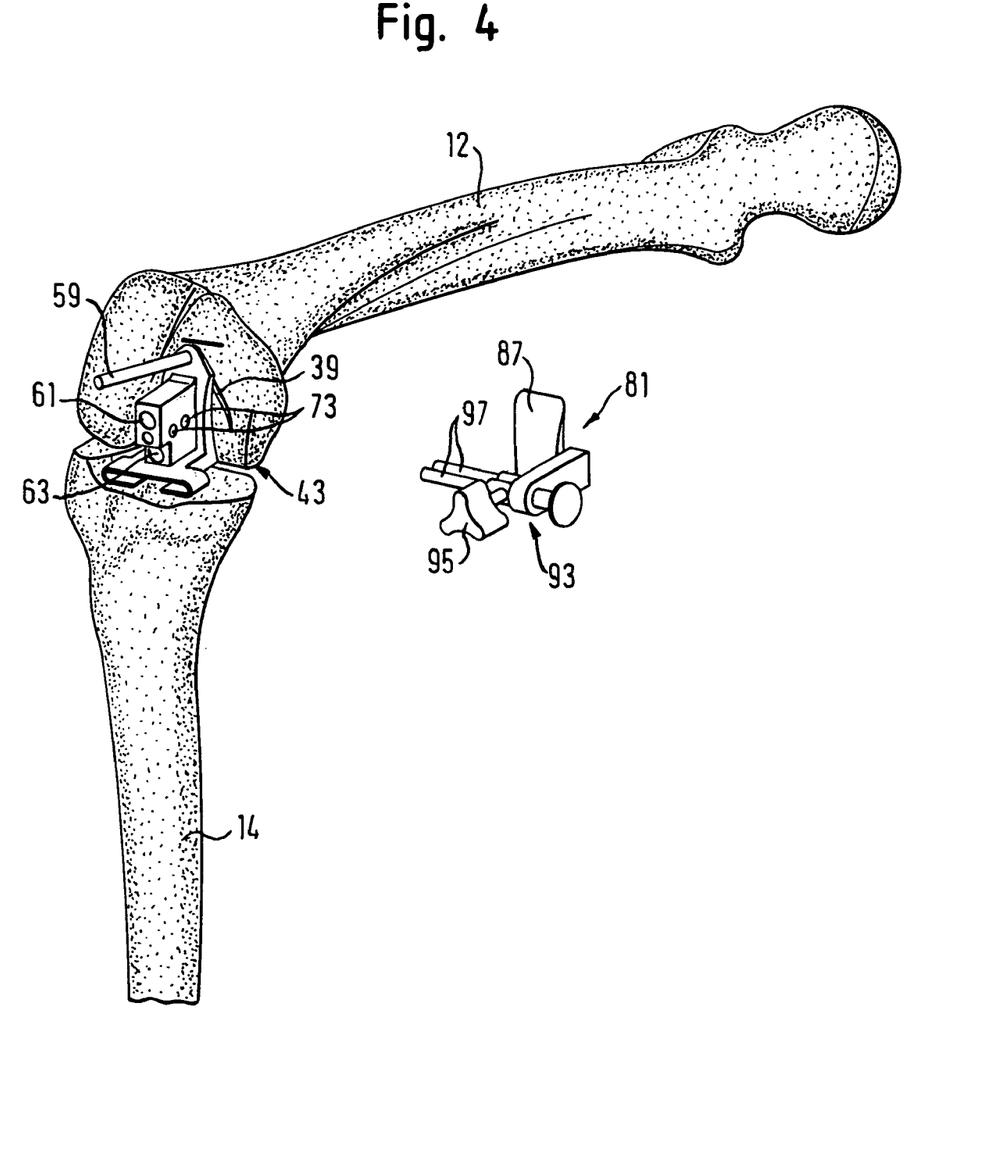
Figure 5:
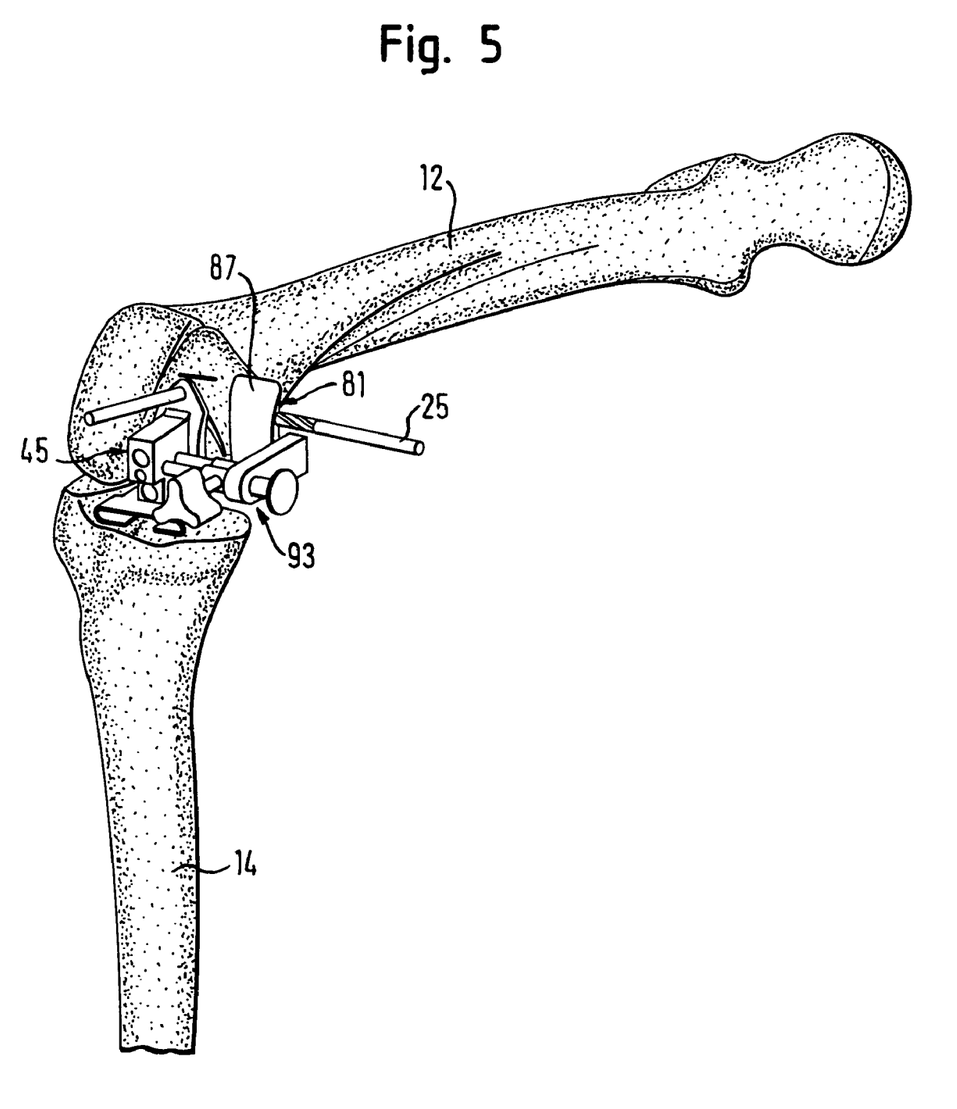

An additional cutting jig 81, which serves to carry out a further condylar cut extending in accordance with the curved side of the jig 45 facing the femoral condyle, is next coupled to the jig 45, which is still fixed to the femoral condyle, via a separate coupling device 93 (cf. FIGS. 4 and 5).

For this purpose, the additional cutting jig 81 is clamped to the coupling device 93 by means of a clamping device 95 of the coupling device 93 and is subsequently coupled to the jig 45 via the coupling device 93 in a defined position relative to the jig 45 in that guide pins 97 of the coupling device 93 are inserted from the side into the already mentioned coupling passages 73 also provided for coupling to the alignment aid 15 (cf. FIG. 2).

The defined relative position mentioned above is characterized in that a guide surface 87 of the cutting jig 81 provided for a cutting tool is oriented with respect to the curve side of the jig 45 in the state coupled to the jig 45 via the coupling device 93 such that the curved side of the jig 45 and the guide surface 87 are only offset to one another translatorily. Consequently, the extent of the curved side of the jig 45 can be transmitted to the femoral condyle via the guide surface 87 in that a cutting tool is moved along the guide surface 87.

Figure 6:
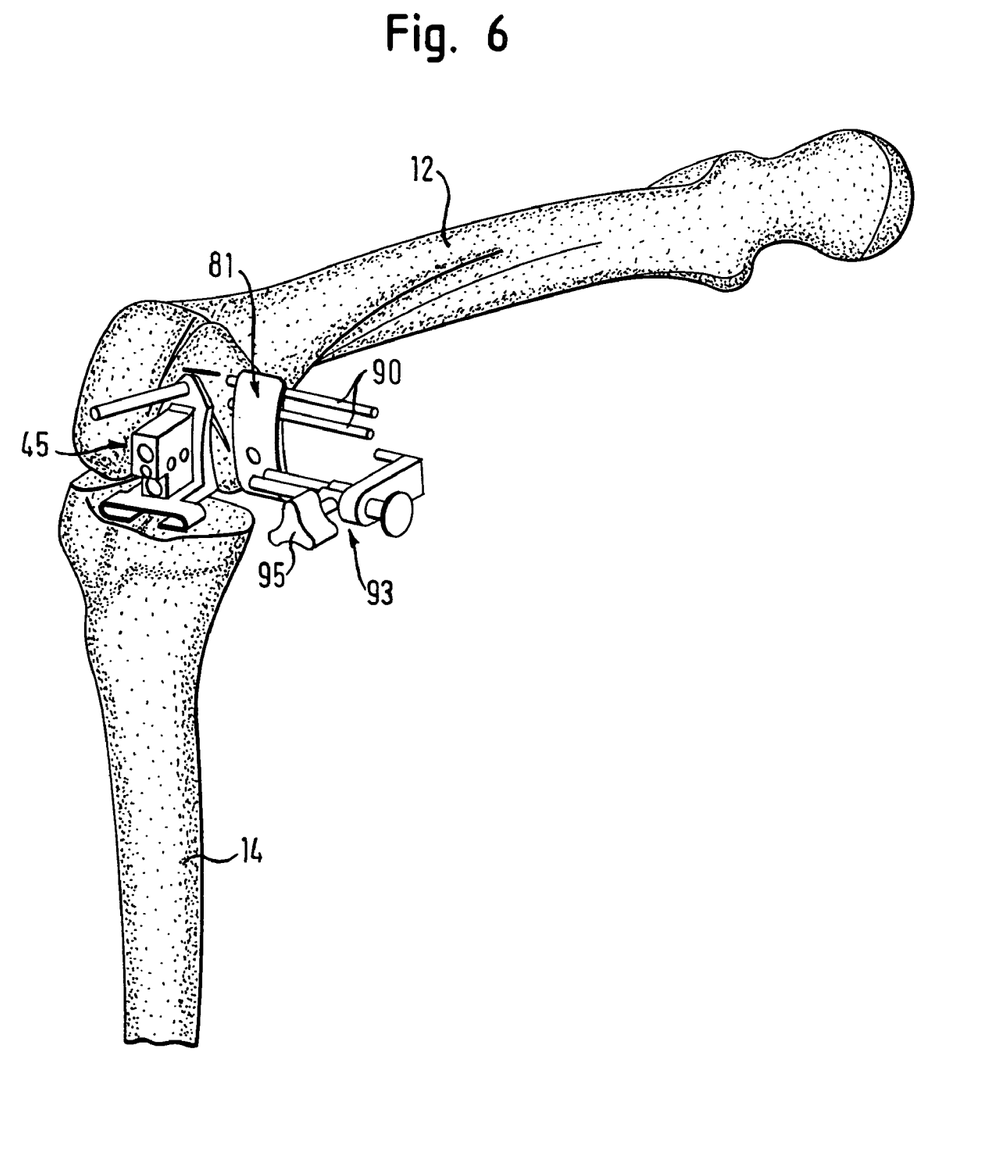

Before the mentioned further condylar cut is carried out in this manner, the additional cutting jig 81 is likewise fixed to the femoral condyle. FIG. 5 shows how the femoral condyle is pre-drilled by means of a drill 25 via fixing passages formed for this purpose in the cutting jig 81 and extending perpendicular to the fixing passages of the jig 45 in the state coupled to the jig 45. FIGS. 6, 7a and 7b show the additional cutting jig 81 in the state fixed to the femoral condyle by means of fixing pins 90 inserted through the fixing passages into the femoral condyle.

The correct position of the additional cutting jig 81 relative to the femoral condyle is thus ensured by the likewise correctly positioned and aligned cutting and drilling jig 45.

The coupling device 93 is subsequently removed, as is indicated in FIG. 6. The combined cutting and drilling jig 45 is then also removed from the femoral condyle.

Before the further condylar cut is carried out with the aid of the guide surface 87 of the cutting jig 81, in accordance with FIG. 7a, the guide surface 87 is adjusted relative to the femoral condyle with the aid of a planar abutment metal sheet 99 and of an adjustment tool 82 until the vertex of the convex guide surface 87 lies in the plane defined by the first condylar cut 39. For this purpose, the abutment metal sheet 99 is inserted into the first condylar cut 39, whereby the cut surface of the first condylar cut 39 is extended and thus an abutment is made available for the guide surface 39.

The adjustability of the guide surface 87 is given in that the cutting jig 81 is made in multiple parts and includes a disk cam 85, at which the guide surface 87 is formed, and a base section 91 which is provided with the fixing passages for the fixing pins 90 and via which the cutting jig 81 is fixed to the femoral condyle.

The setting tool 82 serves for the actuation of an adjustable screw which connects the disk cam 85 and the base section 91 to one another and whose rotational movement effected by means of the setting tool 82 results in a relative movement between the cam disk 85 and the base section 91, whereby the guide surface 87 is moved away from or toward the base section 91.

When the vertex of the guide surface 87 lies in the plane of the first cut surface 39, it is ensured that the femur implant to be inserted is located at the right spacing from the tibia implant to be inserted in every position of the knee joint.

FIG. 7b shows how the curved further condylar cut is carried out by means of a cutting tool in the form of a saw blade 55 guided along the guide surface 87, whereby a curved condylar cut surface 83 is produced between the two previously established condylar cut surfaces 39, 43, whose extent corresponds to the curvature of the curved side of the cutting and drilling jig 45 and thus to the corresponding side of the femur implant to be inserted.

In FIGS. 7a and 7b, the bores 62, 64 can be recognized which are formed in the femoral condyle in connection with the fixing of the combined cutting and drilling jig 45 and into which, on the basis of the forming in accordance with the invention of the drilling section 41 of the jig 45 in accordance with the femur implant to be inserted, the former's spigots can be inserted.

After the curved condylar cut 83 has been carried out, the additional cutting jig 81 is removed from the femoral condyle. The femur implant selected in accordance with the surgery plan can then—optionally after carrying out further preparation steps which should not be considered in more detail here—be fixed to the femoral condyle prepared by means of the apparatus in accordance with the invention.

In accordance with FIG. 8, the combined cutting and drilling jig 45 provided in different sizes corresponding to a set of existing femur implants is formed in the lower region as a cutting jig 37 provided with a slot 57 for a saw blade and in the upper region as a drilling jig 41 which is provided with two fixing passages 69 and through which in each case a drill can be guided for the pre-drilling of the bone and subsequently a fixing element 61, 63 (cf. FIG. 3), in particular a bone screw, can be guided to fix the jig 45 to the femoral condyle.

As already mentioned above, the jig 45 corresponds with respect to the curvature to its concave side 71 facing the femoral condyle during the operation and with respect to the position and to the orientation of the fixing passages 69 with regard to the curved side 71 to a femur implant of the same size. In this respect, the femur implant to be inserted is simulated by means of the jig 45 in the operation.

At its upper end, the jig 45 is provided with a positioning passage 75 through which the positioning pin 59 (cf. e.g. FIG. 3) is guided to hold the jig 45 at the femoral condyle, while the bores 62, 64 for the fixing screws 61, 63 or for the spigots of the femur implant to be inserted are carried out via the fixing passages 69 in the femoral condyle.

Furthermore, the jig 45 is provided in the region between the two fixing passages 69 with coupling passages 73 which extend transversely to the fixing passages 69 and which together form the coupling section 23 of the drilling section 41 of the jig.

The cutting section 37 of the jig 45 is simultaneously made as a slide attachment shoe with which the jig 45 can be attached to the functional attachment 13 of the spreading device 11 (cf. FIG. 1) and can be displaced along the head section of the functional attachment 13.

Figure 9:
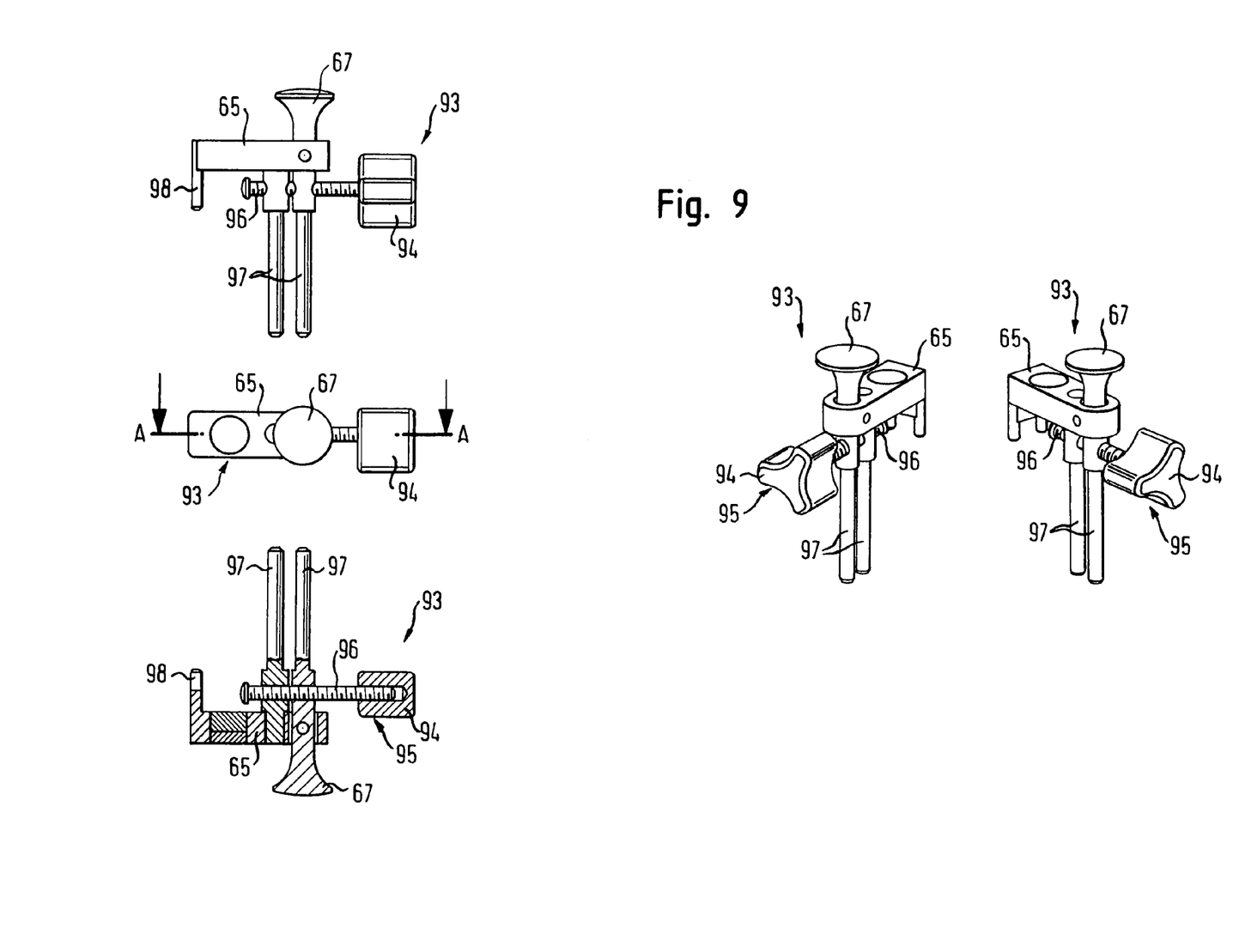
FIG. 9 different views of a separate coupling device in accordance with an embodiment of the invention which can be coupled to the cutting and drilling jig of FIG. 8.

The separate coupling device 93 shown in FIG. 9 includes two guide pins 97 which extend in parallel and are fixedly connected to an outlier 65 which extends perpendicular to the guide pins 97 and which has, at its one end, an abutment section 98 projecting parallel to the guide pins 97. The spacing of the two guide pins 97 corresponds to the spacing of the coupling passages 73 formed in the cutting and drilling jig 45 in accordance with the invention (cf. FIG. 8).

The additional cutting jig 81, which is explained in more detail in the following in connection with FIG. 10, can be clamped in a defined position relative to the coupling device 93 between the abutment section 98 and the free end of a clamping pad 96 which has a handle section 94 and is a component of a clamping apparatus 95 of the coupling device 93. For this purpose, the clamping pad 96 is made as a clamping screw which is rotatable via the handle section 94 and cooperates with the guide pins 97 via a thread.

For the handling of the coupling device 93 on the connection with and on the releasing from the cutting and drilling jig 45, the surgeon can hold the coupling device 93 with the one hand at a radially extended holding end 67 of the one guide pin 97 and can actuate the clamping apparatus 95 via the handle section 94 with the other hand.

Figure 10:
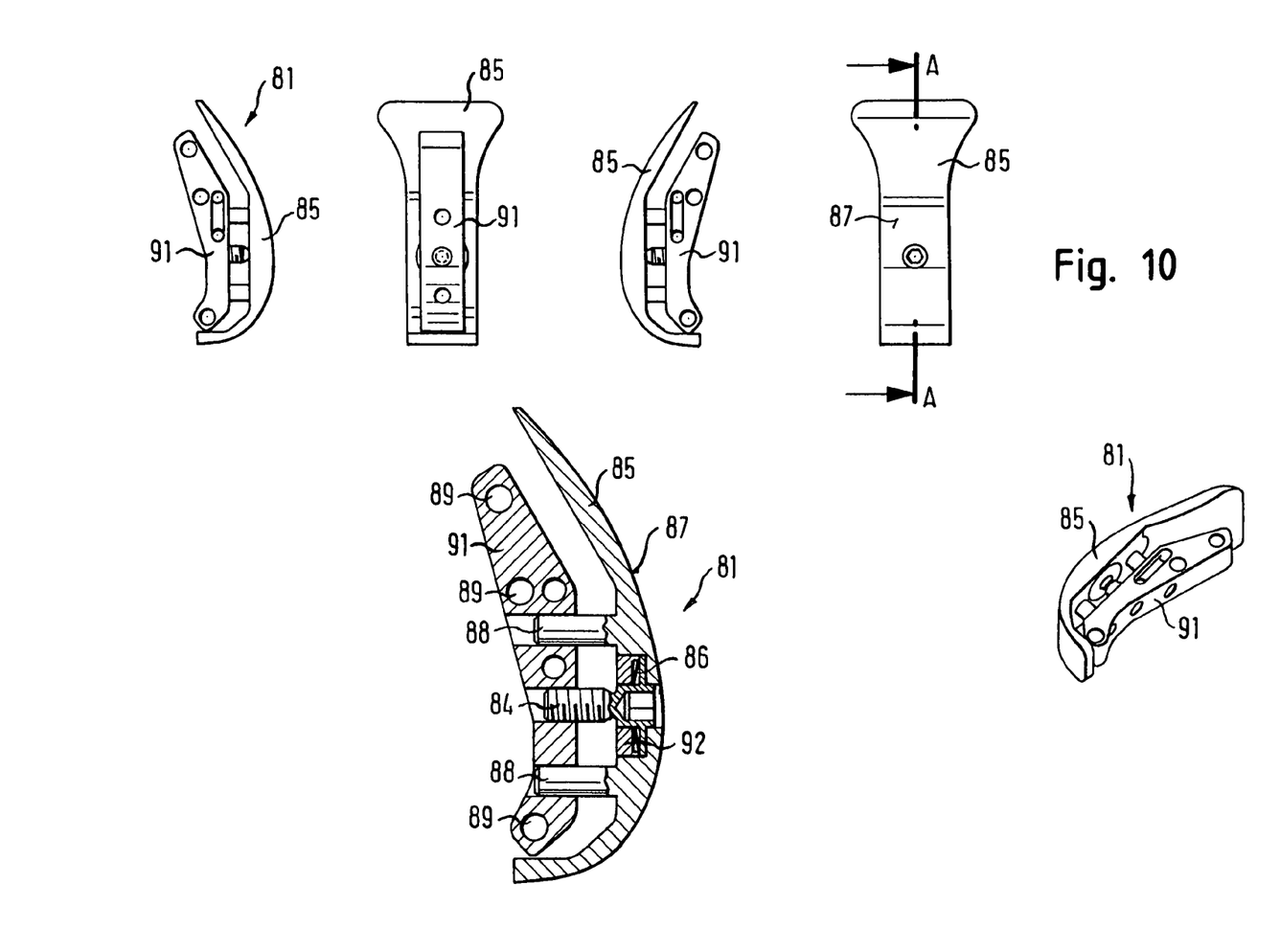
FIG. 10 an additional cutting jig in accordance with an embodiment of the invention which can be coupled to the coupling device of FIG. 9.
Figure 11:
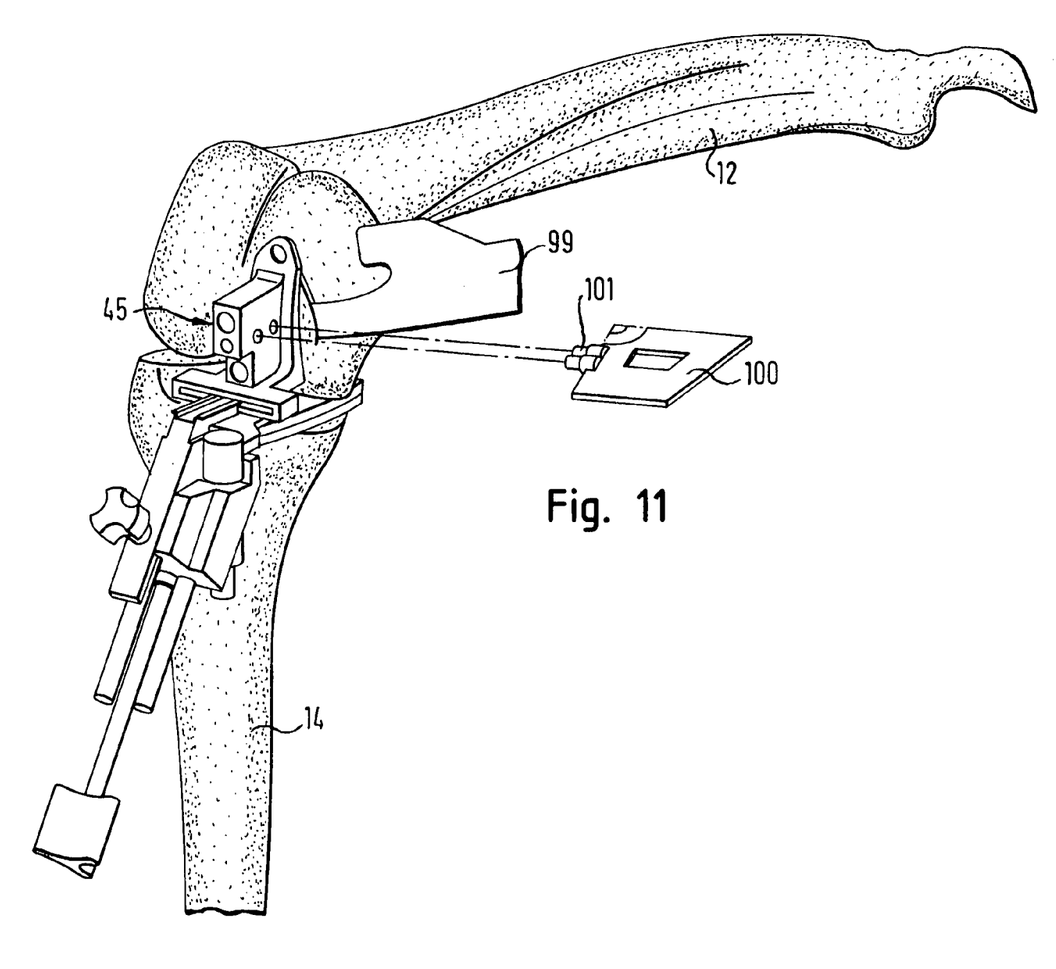

In accordance with FIG. 10, the additional cutting jig 81 provided in accordance with the cutting and drilling jig 45 in different sizes corresponding to the existing femur implant sizes includes a base section 91 which has three fixing passages 89 and relative to which a disk cam 85 provided with the convex guide surface 87 is adjustable. The disk cam 85 is compulsorily guided at the base section 91 via spigots 88 adjustably supported in corresponding passages of the base section 91 such that only a straight-line relative movement is possible between the base section 91 and the disk cam 85.

The adjustment of the disk cam 85 takes place by means of an adjustable screw 84 which cooperates via a shaft provided with an external thread with an internal thread which is formed in a further passage of the base section 91. The ring-shaped head of the adjustable screw 84 is held without clearance in the adjustment direction at the disk cam 85 between the rear side of the disk cam 85 and a spring element 86 formed as a spring washer. The spring washer 86 is supported at a ring-shaped support element 92 which is fixedly connected to the disk cam 85.

The adjustable screw 84 is screwed into or out of the passage of the base section 91 provided with the internal thread by means of the setting tool shown in FIG. 7a and the disk cam 85 is in this manner adjusted relative to the base section 91 in the direction pre-determined by the passages of the base section 91 receiving the spigot 88 or the spigots 88.

As already mentioned, the extent of the convex guide surface 87 of the disk cam 85 corresponds to the concavely curved side 71 of the cutting and drilling jig 45 (cf. FIG. 8) and thus to the corresponding side of a femur implant of the same size to be inserted.

The free end of the clamping pad 96 of the coupling device 93 (cf. FIG. 9) engages, to clamp the additional cutting jig 81, at the opening which is formed in the guide surface 87 and via which the adjustable screw 84 is accessible. For this purpose, the free end of the clamping pad 96 is provided with a rounding.

REFERENCE SYMBOL LIST

11 spreading device
12 femur
13 functional attachment
14 tibia
15 alignment aid
16 adjustment rod
17 lower part
19 upper part
21 actuation member, adjustable screw
23 coupling section
25 drill
27 spreading tongue of the lower part
29 spreading tongue of the upper part
37 cutting section of the jig
39 first condylar cut, first cut surface
41 drilling section of the jig
43 second condylar cut, second cut surface
45 combined cutting and drilling jig
49 fixing device
55 cutting tool, saw blade 57 slot
59 positioning pin
61 fixing element, screw
62 bore
63 fixing element, screw
64 bore
65 outlier
67 holding end
69 fixing passage
71 curved side
73 coupling passage
75 positioning passage
81 additional cutting jig
82 setting tool
83 further condylar cut, curved cut surface
84 adjustable screw
85 disk cam
86 spring element, spring washer
87 guide surface
88 spigot
89 fixing passage
90 fixing pin
91 base section
92 support element
93 separate coupling device
94 handle section
95 clamping apparatus
96 clamping pad
97 guide pin
98 abutment section
99 abutment metal sheet
100 angle metal sheet
101 pin

The invention claimed is:

1. An apparatus for the preparation of a femoral condyle for the insertion of monocondylar knee implants, comprising at least one combined cutting and drilling jig which, when the knee is in flexion, can be fixed to the femoral condyle at a desired spacing from a tibia plateau dependent on the thickness of a tibia implant to be inserted, the jig having concave side facing the femoral condyle and being curved in accordance with a femur implant to be inserted, having at least one fixing passage in a drilling section of the jig for a drill and for a fixing element, with the fixing passage being positioned and oriented with respect to the curved side in accordance with the femur implant to be inserted, having at least one slot in a cutting section of the jig for a cutting tool by which a cutting plane for a condylar cut is defined, and having has a coupling section for an alignment aid by means of which the cutting and drilling jig located at the desired spacing from the tibia plateau is adjustable relative to the femoral condyle.

2. An apparatus in accordance with claim 1, characterized in that at least one coupling passage formed in the drilling section of the jig and extending substantially perpendicular to the fixing passage is provided as a coupling section of the cutting and drilling jig.

3. An apparatus in accordance with claim 1, characterized in that the cutting and drilling jig can be coupled to a spreading device by means of which a desired spacing can be set between the femoral condyle and an oppositely disposed tibia plateau.

4. An apparatus in accordance with claim 3, characterized in that the cutting section of the cutting and drilling jig is simultaneously made as a slide attachment shoe which can be coupled to the spreading device and via which the cutting and drilling jig is adjustable in a compulsorily guided manner at the spreading device.

5. An apparatus in accordance with claim 1 characterized in that the cutting and drilling jig is provided, in addition to the fixing passage, with a positioning passage which is formed in the drilling section of the jig and via which the cutting and drilling jig is positionable relative to the femoral condyle by means of a positioning pin before the fixing to the femoral condyle taking place via the fixing passage.

6. An apparatus in accordance with claim 1 characterized in that the cutting and drilling jig can be coupled to an additional cutting jig with which, when the knee is in flexion, a further condylar cut can be fixed which extends in a curved manner between two planar cut surfaces which have previously been established at the femoral condyle and of which the one out surface was formed by means of the cutting section of the combined cutting and drilling jig and the other cut surface was made when the knee was in extension, with the two planar cut surfaces preferably extending at least substantially perpendicular to one another.

7. An apparatus in accordance with claim 6, characterized in that a course of the curved side of the combined cutting and drilling jig is able to be mapped at least regionally on the femoral condyle by means of the additional cutting jig.

8. An apparatus in accordance with claim 6, characterized in that the additional cutting jig includes a disk cam with a convex guide surface along which a cutting tool is guidable and whose extent corresponds to the curved side of the combined cutting and drilling jig.

9. An apparatus in accordance with claim 8, characterized in that the additional cutting jig is oriented with respect to the cutting and drilling jig in the state coupled to the cutting and drilling jig fixed to the femoral condyle such that the guide surface of the additional cutting jig and the curved side of the cutting and drilling jig are only translatorily offset toward one another.

10. An apparatus in accordance with claim 8, characterized in that the guide surface is adjustable relative to the femoral condyle with the additional cutting jig fixed to the femoral condyle.

11. An apparatus in accordance with claim 8, characterized in that the additional cutting jig includes a base section which can be fixed to the femoral condyle and to which the disk cam is adjustably attached with the base section fixed to the femoral condyle for the alignment of the guide surface formed at the cam disk with a condylar cut which was previously carried out, when the knee was in extension, at a desired spacing from the tibia plateau dependent on the thickness of a tibia implant to be inserted.

12. An apparatus in accordance with claim 11, characterized in that the disk cam is adjustable relative to the base section fixed to the femoral condyle such that the vertex of the guide surface formed at the disk cam is disposed in the plane defined by the condylar cut.

13. An apparatus in accordance with claim 6, characterized in that the additional cutting jig is likewise fixable to the femoral condyle in the state coupled to the cutting and drilling jig fixed to the femoral condyle.

14. An apparatus in accordance with claim 6, characterized in that the additional cutting jig is provided with at least one fixing passage, and preferably a plurality of fixing passages, which extend substantially perpendicular to the fixing passage of the combined cutting and drilling jig in the state coupled to the combined cutting and drilling jig.

15. An apparatus in accordance with claim 6, characterized in that the coupling section of the combined cutting and drilling jig provided for the alignment aid is simultaneously made for coupling to the additional cutting jig.

16. An apparatus in accordance with claim 6, characterized in that a separate coupling device is provided for the coupling of the additional cutting jig to the combined cutting and drilling jig at which the additional cutting jig can be fixed and with which the additional cutting jig is adjustable, in particular linearly displaceable, relative to the combined cutting and drilling jig in the fixed state.

17. An apparatus in accordance with claim 16, characterized in that the coupling device includes a clamping device by means of which the additional cutting jig is fixingly clampable to the coupling device.

18. An apparatus in accordance with claim 16, characterized in that the coupling device is removable with the combined cutting and drilling jig and the additional cutting jig fixed to the femoral condyle.

* * * * *